United States Patent [19]

Grant

[11] 4,277,416
[45] Jul. 7, 1981

[54] PROCESS FOR PRODUCING METHANOL

[75] Inventor: Norman A. Grant, Studio City, Calif.

[73] Assignee: Aminoil, USA, Inc., Huntington Beach, Calif.

[21] Appl. No.: 769,608

[22] Filed: Feb. 17, 1977

[51] Int. Cl.³ .............................................. C07C 31/04
[52] U.S. Cl. ...................... 518/703; 48/210; 60/39.02; 60/39.12; 406/197; 564/63
[58] Field of Search .......... 302/66; 48/197 R, 196 A, 48/210; 260/449.5, 555 R; 60/39.02, 39.12, 39.18 B; 252/373

[56] References Cited

U.S. PATENT DOCUMENTS

| | | | |
|---|---|---|---|
| 2,256,333 | 9/1941 | Wilcox et al. | 252/373 |
| 2,383,715 | 8/1945 | DeJohn | 252/373 |
| 2,697,606 | 12/1954 | Moses et al. | 48/197 R |
| 3,551,123 | 12/1970 | Stotler | 48/197 R |
| 3,598,527 | 8/1971 | Quartulli et al. | 260/449.5 |
| 3,804,606 | 4/1974 | Archer | 48/206 |
| 3,849,662 | 11/1974 | Blaskowski | 60/39.18 B |
| 3,920,717 | 11/1975 | Marion | 260/449.5 |
| 3,926,203 | 12/1975 | Marsden | 302/66 |
| 3,962,300 | 6/1976 | Hiller et al. | 260/449.5 |
| 3,968,999 | 7/1976 | Keller | 302/66 |
| 3,986,349 | 10/1976 | Egan | 60/39.18 B |
| 4,027,688 | 6/1977 | Gruber | 302/66 |

FOREIGN PATENT DOCUMENTS 1494555  9/1967  France .................. 260/555 R

OTHER PUBLICATIONS

"The Lurgi Low Pressure Methanol Process", Hiller et al., Chemical Economy & Eng. Review 9-1971.

*Primary Examiner*—Peter F. Kratz
*Attorney, Agent, or Firm*—Knobbe, Martens, Olson, Hubbard & Bear

[57] ABSTRACT

A system for processing coal to produce methanol, alcohol-slurry coal for transport, electric power and urea. Raw coal is graded. The downgraded fraction is gasified, producing steam and synthesis gas. The synthesis gas is converted to methanol which is then used to slurry upgraded coal for transport or to produce electric power. The steam output of the gasifier drives an oxygen generator to produce oxygen for the gasifier, when the synthesis gas is used to produce methanol, and also drives an electric power turbine. Natural gas may be used to maximize methanol production. Urea is a by-product.

9 Claims, 2 Drawing Figures

PROCESS FOR PRODUCING METHANOL

BACKGROUND OF THE INVENTION

This invention relates to a method and process for converting raw coal efficiently to its finished products. Raw coal is processed through a sequence of steps into usable end products and electrical energy.

Large deposits of raw coal in many areas of the world are relatively inaccessible to large population and industrial centers where the coal can be readily utilized. Transportation of the coal from these areas, mining costs, and similar economic factors have limited the exploitation of these resources. In the United States alone, large deposits, especially in Alaska, have not been the subject of extensive mining because of economic and transportation difficulties inherent in any attempt to exploit these resources. Accordingly, a process for converting coal into products which can be economically shipped from a point located at or near the mining site has increasingly been desired.

The prior art discloses numerous methods for processing coal, including gasification, and methods of transportation, including various methods for creating coal slurries, see References 1-2. However, a workable system integrating into one economic unit means capable of exploiting these remote coal resources has not been accomplished. Additionally, restraints are placed on the exploitation of coal in that any process utilizing coal must meet modern environmental and pollution standards. A processing system capable of economically exploiting remote coal resources in an environmentally acceptable fashion is described and claimed herein.

BACKGROUND REFERENCES

The following references are incorporated into the disclosure of this patent by reference:
1. Howard-Smith, I., and Werner, G. J., *Coal Conversion Technology*, Noyes Data Corporation, Park Ridge, N.J., 1976.
2. Kirk-Othmer ENCYCLOPEDIA OF CHEMICAL TECHNOLOGY, 2nd Ed., Supplement 1971, pp. 177-249, "Coal".
4. Kirk-Othmer ENCYCLOPEDIA OF CHEMICAL TECHNOLOGY, 2nd Ed., Vol. 5, pp. 606-678, "Coal".
3. Kirk-Othmer ENCYCLOPEDIA OF CHEMICAL TECHNOLOGY, 2nd Ed., Vol. 10, pp. 353-442, "Gas, Manufactured".
5. U.S. Pat. No. 2,716,598, Moses.
6. U.S. Pat. No. 2,851,346, Sprague.
7. U.S. Pat. No. 2,864,560, Carkeek et al.
8. U.S. Pat. No. 2,924,515, Chapman et al.
9. U.S. Pat. No. 3,519,552, Hellwig.
10. U.S. Pat. No. 3,692,506, Johnson.
11. U.S. Pat. No. 3,746,522, Donath.
12. U.S. Pat. No. 3,817,723, Donath.
13. U.S. Pat. No. 3,840,354, Donath.
14. U.S. Pat. No. 3,856,658, Wolk et al.
15. Pat. No. 156,950 (Australian), Texaco Development Corporation.
16. Kirk-Othmer ENCYCLOPEDIA OF CHEMICAL TECHNOLOGY, 2nd Ed., Vol. 21, pp. 37-56, "Urea".
17. Richardson, F. W., *Oil from Coal*, Noyes Data Corporation, 1935.
18. Kirk-Othmer ENCYCLOPEDIA OF CHEMICAL TECHNOLOGY, 2nd Ed., Vol. 13, pp. 370-398, "Methanol".

SUMMARY OF THE INVENTION

Raw coal is refined by prior art methods into an upgraded fraction of coal and one of a downgraded quality. The downgraded fraction is passed through a hot gasifier. The gasifier has as inputs coal and either oxygen or air. The exothermic reaction of coal with oxygen in the gasifier yields internally generated hydrogen and steam and also produces a high temperature gas stream. The net excess heat in the gas stream is converted to a medium grade steam which is put to three terminal uses:
  A. The steam is upgraded by superheating and used to drive a base load turbine for the production of electrical power which may be used locally and consumed by the local utilities.
  B. Steam is also used to drive an oxygen generator to supply oxygen back to the gasifier.
  C. Steam output from the gasifier can be used by a natural gas converter if there is a source of natural gas located in the vicinity of the coal deposit.

The second main output of the gasifier is a synthesis gas. The principal constituents of this synthesis gas are carbon monoxide (CO) and hydrogen gas ($H_2$). This gas output is a highly desirable, non-polluting fuel which can be used directly to power a gas turbine and thence to produce electric power. The system thus includes two sets of generators, gas-fired turbines powered by the synthesis gas and the base steam-powered turbines driven by upgraded steam from the gasification process.

Additionally, the synthesis gas is converted into a methanol base fuel. Since the gas coming from the gasifier is relatively deficient in hydrogen content, it is especially efficient to use the synthesis gas together with gas from a natural gas converter to produce methanol base fuel, since the converter gas consists of carbon monoxide heavily impregnated with hydrogen. The methanol base fuel, which is a mixture of methanol, higher alcohols and water, is slurried with the upgraded coal fraction.

The upgraded coal fraction from the refinery is dried and dehydrated after upgrading because it is uneconomical to ship the coal in its undehydrated form. Medium and low grade heat from electric power generation may be used to dry the coal. The dry, upgraded coal is then slurried with the alcohol, this prevents rehydration of the coal and forms, while in transit, a slurry which is readily transportable by pipeline or in tankers to ultimate consumer centers. This is especially economical inasmuch as the alcohol itself forms a useful fuel along with the coal. Furthermore, all but chemically bonded water is removed from the coal by the alcohol and the low heat value of the slurried coal approaches the high heat value which is usually unattainable.

When the synthesis gas from the gasifier is used to produce methanol base fuel, it is desirable to run the gasifier with pure oxygen rather than air, since the nitrogen in the air is an undesirable impurity in the production of the methanol base fuel. A by-product of the oxygen production is nitrogen. This nitrogen may be combined with the synthesis gas or purge gases from the methanol fuel plant, which contain carbon dioxide, to produce urea.

Preferably, the oxygen generator is powered by steam from the gasifier. When all the synthesis gas from the gasifier is diverted from methanol fuel production to electric power generation, the oxygen generator may be shut down and the steam normally used to power the oxygen generator can also be diverted to the steam driven generator to produce additional electric power. Thus, the process can supply a very wide range of electric power demands in the local area; the synthesis gas can be modulated between methanol fuel production and electric power production as local electric power requirements vary, in excess of the power supplied by the base steam generator, and the energy used to generate the oxygen can also be easily diverted to electrical power production.

The advantages of the instant invention are numerous. An integrated system economically converts coal into readily transportable and usable products. The products include a high grade coal slurry, an electrical power system which is capable of meeting widely varying power demands, and the conversion of by-products into useful, saleable by-products. In addition, the process is capable of using natural gas in combination with coal products to produce a high energy fuel which is safely transportable by conventional means at a fraction of gas transport costs. This latter advantage is especially useful in areas which have natural gas fields near coal fields, as is the case in Alaska.

DETAILED DESCRIPTION OF THE PREFERRED EMBODIMENT

Figure 1:
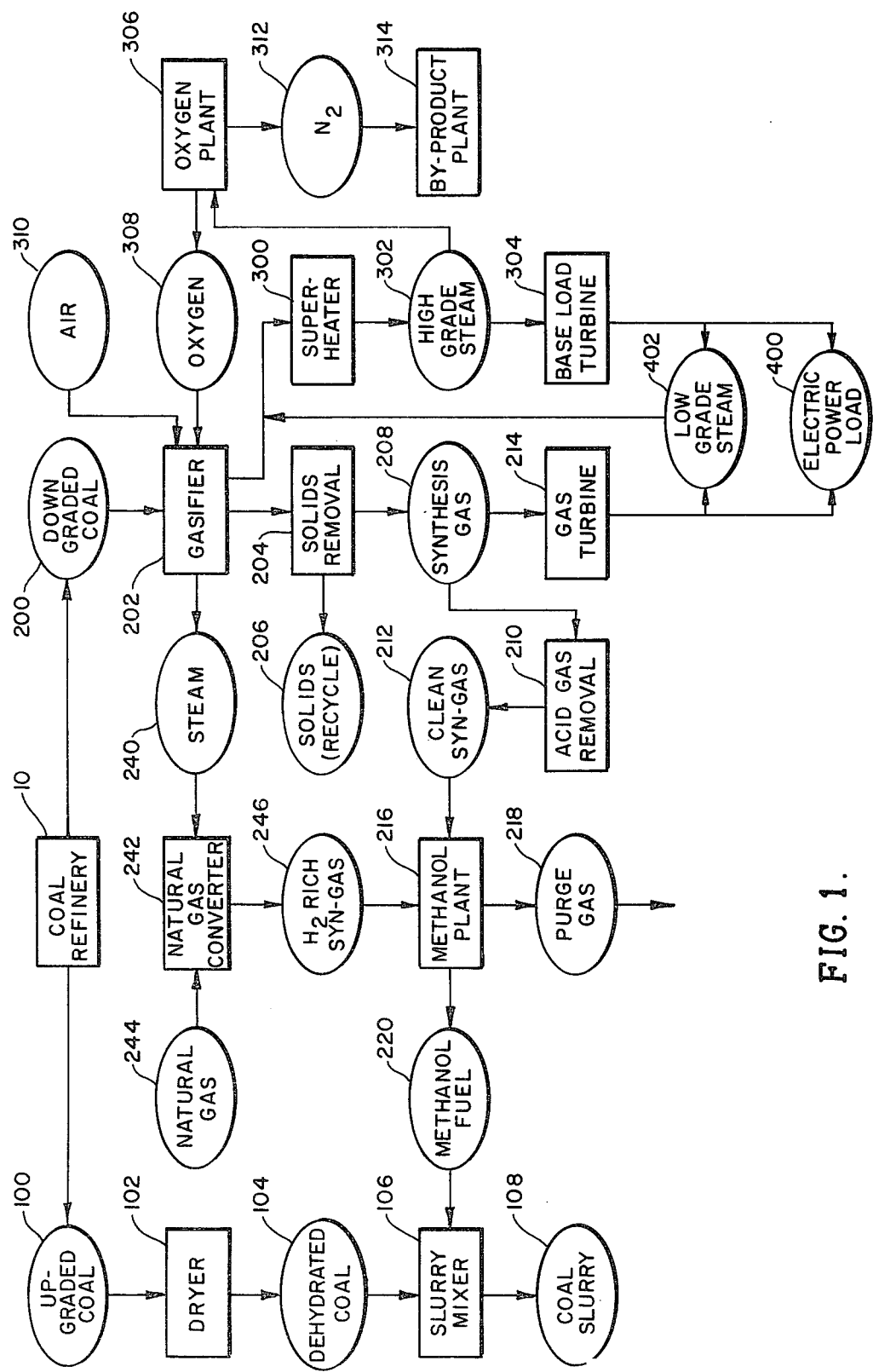
FIG. 1 is a block schematic flow chart of the disclosed process.

Referring now to FIG. 1, raw coal is mined in a conventional manner and is crushed, ground and water-slurried to keep it from losing volatiles that are present in the coal, and refined. (References 1,2) The output of this refinery 10 is threefold. It produces waste tailings, an upgraded fraction of coal 100 and a downgraded fraction of coal 200.

The upgraded fraction of coal 100 is treated in a conventional drier 102 to produce dehydrated coal 104. The dehydrated coal 104 is slurried with alcohol in a mixer 106 by well known processes (5), to form an alcohol-coal slurry 108 which is easily and safely transportable by pipeline, using conventional slurry pumping and handling equipment, by tanker without the need for high pressure vessels, cryogenic equipment or other high-cost transportation facilities. The alcohol-coal slurry can be used as a single fuel blend, since both the solid and liquid components of the fuel are high energy fuel sources. Alternatively, at the destination the components can be separated and used separately as fuels or feedstocks for the chemical process industry in the production of industrial chemicals. As will be described in greater detail hereinafter, the "alcohol" component may be refined to consist essentially of methanol; however, greatest on-site efficiency and maximum fuel value recovery is achieved by producing a fuel blend which includes methanol as its major constituent with minor amounts of higher alcohols, some water and traces of ethers and other alcohol reaction products. This fuel blend is referred to in this patent as "methanol based fuel" or simply as "methanol fuel".

Process heat for on-site treating of the coal and the downgraded coal fraction 200. The downgraded coal fraction 200 is gasified in a conventional gasifier (1, 2, 3, 4), preferably the "Texaco" type gasifier (15) to produce both heat and synthesis gas. The coal fed to the gasifier 202 in the form of a preheated water slurry and reacted with air, oxygen, or oxygen enriched air, at from about 2,000° to 3,000° F. The reaction temperature and the output of the gasifier is modulated by controlling the oxygen/air input using conventional process monitoring and control equipment. Solids are removed from the output gas using conventional particulate matter removal means 204. The solid particulate matter 206 is typically recycled to the input of the gasifier 202. Solids are removed from the gasifier output by a cyclone, Cotrell precipitator or other solid particulate removal means 204. The solids 206 are recycled to the gasifier input. The synthesis gas is then scrubbed or treated in a conventional acid gas ($CO_2$, $SO_2$, etc.) removal plant 210 to produce a clean synthesis gas stream 212.

The clean synthesis gas 212 consists essentially of carbon monoxide, carbon dioxide, hydrogen and water vapor; however iron oxide or other methanization catalyst may be included in the gasifier 202 in which case the synthesis gas will also include methane (3,15).

The other usable output of the gasifier is saturated steam of medium to high quality. This steam, generated by heat exchange in the gasifier and with the gasifier product stream, may be used directly but is most effectively used after superheating with a separately fired superheater 300, which may be fixed by purge gas from the methanol fuel synthesis process, described hereinafter, or any other available fuel source, such as natural gas, synthesis gas or even methanol fuel, as may be required to supplement purge gas as a source of additional heat and produce a stream of high grade steam 302.

High grade steam 302 is a relatively constant energy source resulting from the process and system of this invention and can efficiently be utilized to drive a steam turbine 304 to produce a base electric power load required for operation of a community or other electric utility or to be supplied into an electric power grid as a base load source 400 of electric energy. Low grade steam 402 from the base load generator may be recycled to the superheater 300 or diverted as process heat for other parts of the overall process. For example, some or all of the low grade heat 402 may be used to dry the upgraded coal fraction 100.

Heat from the gasifier may be used directly or, as indicated in FIG. 1, superheated to drive the oxygen plant 306 to provide a stream of relatively purge oxygen 308 to the gasifier 202. Air 310 from any convenient source is also supplied to the gasifier 202. Operation and output of the gasifier is modulated in part by the feed of air 310 or oxygen 308 or oxygen enriched air from both sources. Nitrogen 312 is a by-product of the oxygen plant. By-product nitrogen may be used in a number of ways or compressed and sold. For example, the purge gas from the methanol plant is a ready source of carbon dioxide and, together with the nitrogen stream 312, provides the two major feedstocks for a urea plant which, as indicated at 314, is a particularly advantageous by-product of the overall product. Urea is a valuable industrial intermediate used in the manufacture of resins, fertilizers and many other industrial chemicals and saleable end and intermediate products. The by-product could be ammonia when natural gas or other sources of hydrogen are available. Many other by-products can be manufactured from nitrogen.

The synthesis gas 208, composed principally of carbon monoxide and hydrogen, is a high grade, non-polluting fuel which can be burned to drive a gas turbine generator 214. This gas turbine generator 214 can either permanently augment the base steam turbine generator 304 to supply electricity 400 to local consumers, or it can be used as a back-up generator for peak periods when electrical demands exceed the capacity of the base steam turbine system 304.

The clean synthesis gas stream 212 is supplied to a conventional methanol plant 216 (18) since the content of this gas, carbon monoxide and hydrogen, is highly suitable for processing into methanol. The synthesis gas stream may be passed through a conventional shift reactor to yield the desired $CO-H_2$ content. If the synthesis gas 212 is used to produce methanol, then the gasifier 202 should have as its input pure oxygen 308 instead of air 310 to eliminate nitrogen, which is undesirable in the methanizer, as an impurity. In this case, the oxygen generator 306 is conveniently powered by using part of the steam output from the gasifier 202. Nitrogen 312 from the generation of oxygen can be used by a urea plant to manufacture urea or other nitrogen based by-products.

When all of the synthesis gas 208 is supplied completely to the gas turbine 214, then the oxygen generator 306 is shut down, and the steam which is normally supplied to it is fed to the base steam turbine generator 304, providing additional peak power to the electric supply system. Because of the high temperature and high pressure of this "low BTU" gas and because of the relatively high proportion of hydrogen in the stream 208, this gas provides an excellent pollution free fuel for commercial turbines.

Part of the steam from the gasifier, as indicated at 240, can be supplied to a natural gas converter 242, where it is reacted with natural gas 244 to yield a stream 246 of hydrogen rich synthesis gas which consists principally of one part carbon monoxide gas with three parts hydrogen. (18) This hydrogen rich gas supplied to the methanol plant along with the synthesis gas 212 from the gasifier 202 provides maximum production of methanol, optimum utilization of the carbon in the natural gas and in coal, resulting in a maximum retention of available carbon in the liquid fuel product and a minimum conversion of carbon to carbon dioxide in the gasifier, thus reducing oxygen requirements in the overall process. The use of the natural gas converter is especially desirable because natural gas is relatively high in hydrogen content while the gas from the gasifier is relatively rich in carbon monoxide content. Thus, by combining these two in balanced proportions, a maximum output of methanol can be achieved, thereby resulting in a highly efficient production of methanol. The alcohol output of the methanol plant 216 is combined with the upgraded dehydrated coal in a conventional mixer 106 forming a coal-methanol fuel 108 slurry. This fuel is easily transportable and storeable. Dehydrated to an optimum degree, excess weight to be shipped in the fuel is materially reduced. The slurry fuel product is, therefore, economically transported. Presently available data indicate a shipping cost/BTU of about one-sixth the shipping cost of the gas by the proposed arctic pipeline.

The upgraded coal fraction 100 may conveniently use low grade heat 402 from the electric power generation to aid in drying the upgraded coal in the dryer 102. Thus, even the waste heat is put to an economical use in this system.

The process described herein is especially flexible in that it enables adjustment to variations in local electric power demand. The synthesis gas may be diverted, in varying amounts, from methanol production to electrical energy production and back to methanol production in response to demands by local utilities for electrical energy that are in excess of the capacity of the base steam turbine generator. In the event the entire synthesis gas output is used to drive the gas turbine, air may be used as the input to the gasifier and steam which otherwise would power the oxygen generator may be directed to the base steam turbine to further augment its electric output. When it is desired to divert some or all of the gas to methanol production, steam can again be diverted to the oxygen generator and pure oxygen used as the gasifier input.

Figure 2:
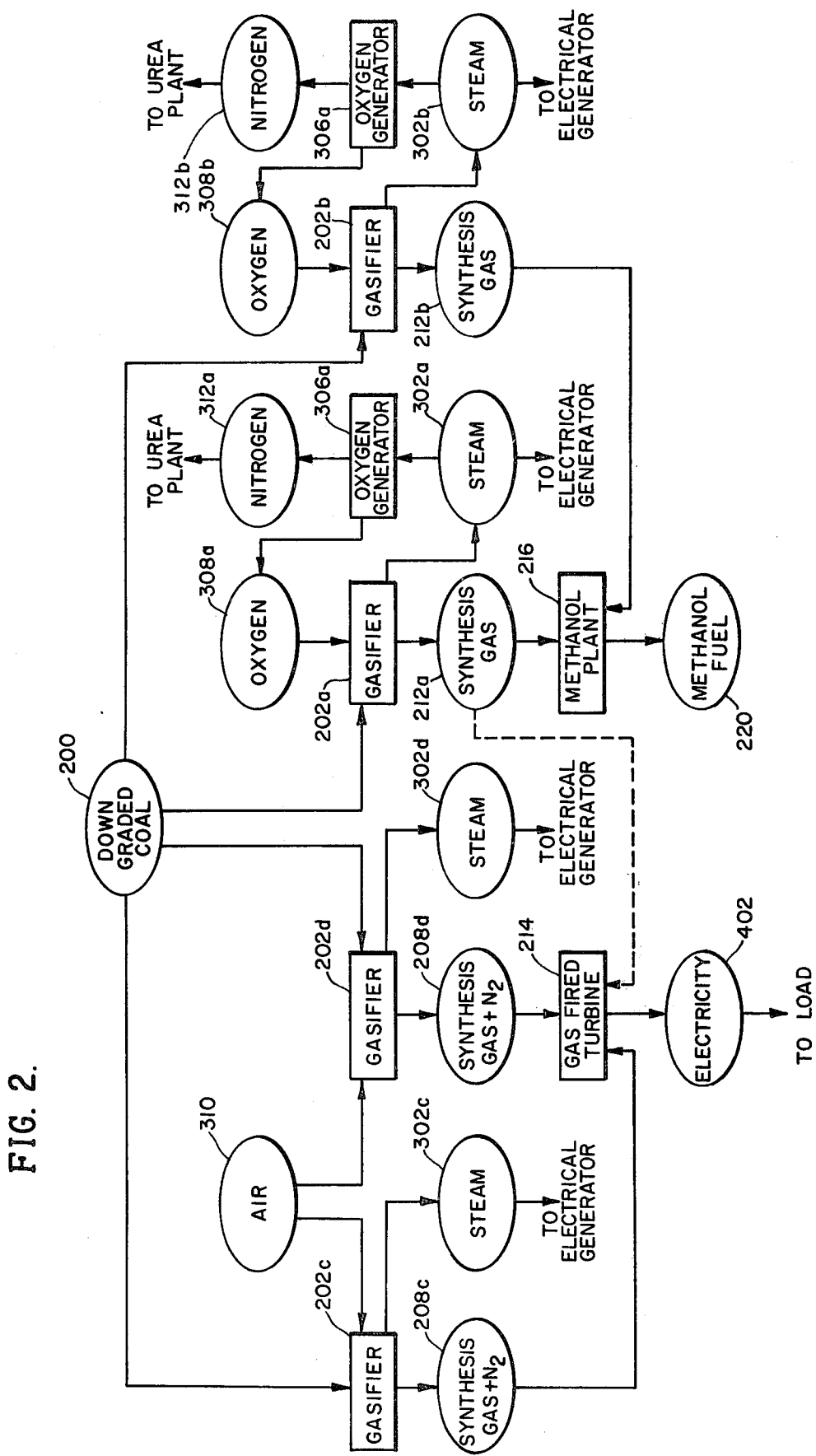
FIG. 2 is a flow chart of the process with multiple gasifiers.

In a typical system and process several gasifiers are teamed together to provide maximum flexibility in meeting demands for electric energy and for producing methanol fuel in quantities sufficient to slurry all upgraded coal for transport. Such a system may typically include ten or more gasifiers. FIG. 2 depicts a system of this type on small scale, schematically, wherein only four gasifiers are ganged together. This system illustrates some of the great flexibility available in the present invention. Gasifiers 202a and 202b, on the right of the drawing, are operating to maximize methanol fuel production, using oxygen 308a and 308b from oxygen plants 306a and 306b, powered by steam 302a and 302b from the gasifiers, as the feed source. By-product nitrogen 312a and 312b, being produced in relatively high quantities in this operational mode, is being converted to urea by reaction with carbon dioxide from the methanol plant 216 into which all synthesis gas 212a and 212b is fed. Steam from the gasifier 302a and 302b is superheated, as shown in FIG. 1 but omitted for simplicity in FIG. 2, drives the base load turbine to meet a predetermined minimum demand for electricity. At the same time, gasifiers 202c and 202d are being fed with air 310 to produce steam 302c and 302d which drive base load generators and high nitrogen content synthesis gas 208c and 208d which is burned to produce a high grade gas stream to drive gas fired turbine 214 to meet an electric demand above the base load. As the demand for power increases, first one and then another of gasifiers 202a and 202b may be fed with air to increase peak load generation capacity—with the consequence that methanol fuel production decreases. Conversely, as electric power demand subsides, one after another of gasifiers 202a, 202b, 202c and 202d is oxygen fired to maximize methanol fuel production while still maintaining base load electricity generation capacity. By ganging ten or twenty gasifiers in the manner described, extreme flexibility in electric power generation capacity for peak load demand and maximum methanol production during off-peak power demand periods is accomplished.

Upon increased demand for electricity, some synthesis gas from one or more gasifiers is diverted to the gas turbine for electric power generation. Upon further demand air is fed to the gasifier and the entire synthesis gas and steam output of the gasifier is diverted to electrical power generation. As electric power demand drops this process can be reversed. In this fashion, end products can be continuously manufactured, without sacrificing the system's ability to flexibly meet varying electric power demands.

The great flexibility of this system is readily apparent. The system may be adjusted to provide varying amounts of electric power, methanol, and by-product, e.g., urea, as required at any given time. Also, the system produces a coal slurry transport of very high quality which is economical to store and transport. Finally, this processing system is extremely efficient in its use of raw materials; the coal is converted to useful end products with great efficiency and very little waste. The energy produced in this system is efficiently converted to electrical power, and the waste heat from this production can even be recovered to help dry the coal, resulting in very efficient energy usage by the system.

Environmentally, the process of the invention is highly acceptable. The saleable products are electric energy, sulfur-free methanol fuel, essentially sulfur free coal, elemental sulfur, and urea. Waste products are non-polluting carbon dioxide, nitrogen, water and glass slag.

One significant advantage of the invention is that a 3:1 leverage on the use of natural gas is obtainable; i.e. by using 1 BTU of natural gas, 4 BTU of methanol fuel-coal slurry is economically transported.

What is claimed is:

1. A process for converting coal to varying end products comprising:
   gasifying coal in a plurality of gasifiers to produce a synthesis gas and heat;
   converting at least part of said heat through a heat exchanger into steam;
   directing during some time periods at least part of said synthesis gas to a methanol plant;
   during the aforesaid time period inputting oxygen from an oxygen generator into at least some of the gasifiers;
   inputting air during other time periods to said gasifiers;
   directing at least part of the steam output from gasification to a steam turbine generator to produce electricity;
   directing part of the steam from gasification to drive said oxygen generator during the first said time period when oxygen is used as a gasifier input; and
   directing the entire steam output from gasification steam to said electric power generation during said other time period when air is used as the gasifier input.

2. The process of claim 1 in which a part of the synthesis gas which is not directed to a methanol plant is directed to a gas turbine generator during the first said time period when some but not all of the synthesis gas is directed to a methanol plant.

3. The process of claim 1 in which said coal for gasifying is a downgraded fraction of coal from a coal refinery.

4. The process of claim 1 in which waste heat from the steam generator is used to dry an upgraded fraction of coal from a coal refinery.

5. The process of claim 2 in which waste heat from said steam turbine generator and said gas turbine generator is used to dry an upgraded coal fraction from a coal refinery.

6. The process of claim 1 in which nitrogen from said oxygen generator is used with purge gases from the methanol plant to produce urea.

7. The process of claim 1 in which nitrogen from said oxygen generator is used with a part of the synthesis gas not directed to a methanol plant to form urea.

8. The process of claim 1 including:
   diverting steam from said heat exchanger to a natural gas converter when synthesis gas is directed to a methanol plant; and
   using the hydrogen rich synthesis gas from the natural gas converter as an input to the methanol plant along with said coal gasifier synthesis gas.

9. The process of claim 8 in which the output of the natural gas converter is balanced with the gasifier synthesis gas fed to the methanol plant to maximize the production of alcohol.

* * * * *